(12) United States Patent
Berberich et al.

(10) Patent No.: US 11,311,283 B2
(45) Date of Patent: Apr. 26, 2022

(54) SUTURING DEVICE, IN PARTICULAR FOR SUTURING LACERATIONS OF THE MENISCUS

(71) Applicant: MEDACTA INTERNATIONAL SA, Castel San Pietro (CH)

(72) Inventors: Sascha Berberich, Castel San Pietro (CH); Francesco Siccardi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 141 days.

(21) Appl. No.: 16/339,185

(22) PCT Filed: Oct. 2, 2017

(86) PCT No.: PCT/IB2017/056062
§ 371 (c)(1),
(2) Date: Apr. 3, 2019

(87) PCT Pub. No.: WO2018/065878
PCT Pub. Date: Apr. 12, 2018

(65) Prior Publication Data
US 2019/0231339 A1    Aug. 1, 2019

(30) Foreign Application Priority Data
Oct. 6, 2016   (IT) .................. 102016000100552

(51) Int. Cl.
*A61B 17/04*   (2006.01)

(52) U.S. Cl.
CPC ...... *A61B 17/0401* (2013.01); *A61B 17/0469* (2013.01); *A61B 2017/0403* (2013.01); *A61B 2017/0408* (2013.01); *A61B 2017/0409* (2013.01); *A61B 2017/0414* (2013.01); *A61B 2017/0464* (2013.01)

(58) Field of Classification Search
CPC ............ A61B 17/0401; A61B 17/0469; A61B 2017/0408; A61B 2017/0409;
(Continued)

(56) References Cited

U.S. PATENT DOCUMENTS

2004/0153074 A1* 8/2004 Bojarski ............ A61B 17/0401
606/232
2008/0255613 A1* 10/2008 Kaiser .............. A61B 17/06166
606/232

(Continued)

FOREIGN PATENT DOCUMENTS

AU       2015202757 A1   6/2015
DE       202015002244 U1  6/2016
(Continued)

OTHER PUBLICATIONS

English Translation of Notice of Reasons for Refusal issued in JP 2019-518410, dated Mar. 6, 2020, 8 pages.
(Continued)

*Primary Examiner* — Kelly J Bekker
*Assistant Examiner* — Andrew P. Restaino
(74) *Attorney, Agent, or Firm* — Meunier Carlin & Curfman LLC

(57) ABSTRACT

A suturing device, in particular for suturing lacerations of the meniscus, comprises an elongated body provided with a longitudinal cavity extending along a main direction, at least a first and a second implant slidably inserted in the cavity and arranged in sequence along the main direction and a surgical thread slidably inserted in the cavity and connected to the first and second implant. Such first and second implant comprise, respectively, a first and a second wedge-shaped element arranged in sequence and extending from an enlarged portion to a tapered portion along the main direction.

6 Claims, 3 Drawing Sheets

(58) Field of Classification Search
CPC ..... A61B 2017/0414; A61B 2017/0403–0464; A61B 2017/0472; A61B 2017/0477; A61L 27/3654; A61L 27/3852; A61F 2/3872
See application file for complete search history.

(56) References Cited

U.S. PATENT DOCUMENTS

| | | |
|---|---|---|
| 2012/0228355 A1 | 9/2012 | Combrowski et al. |
| 2014/0200587 A1 | 7/2014 | Pompee et al. |
| 2015/0250470 A1* | 9/2015 | Vargas ............... A61B 17/0401 606/232 |
| 2018/0055506 A1 | 3/2018 | Weber et al. |

FOREIGN PATENT DOCUMENTS

| | | |
|---|---|---|
| EP | 2474271 A2 | 7/2012 |
| JP | 2003515379 A | 5/2003 |
| JP | 201235089 A | 2/2012 |
| WO | 0139671 A1 | 6/2001 |
| WO | 2004062459 A2 | 7/2004 |
| WO | 2013004947 A1 | 1/2013 |

OTHER PUBLICATIONS

International Search Report and Written Opinion for Application No. PCT/IB2017/056062. International Searching Authority, European Patent Office, dated Jan. 23, 2018. 11 pages.

* cited by examiner

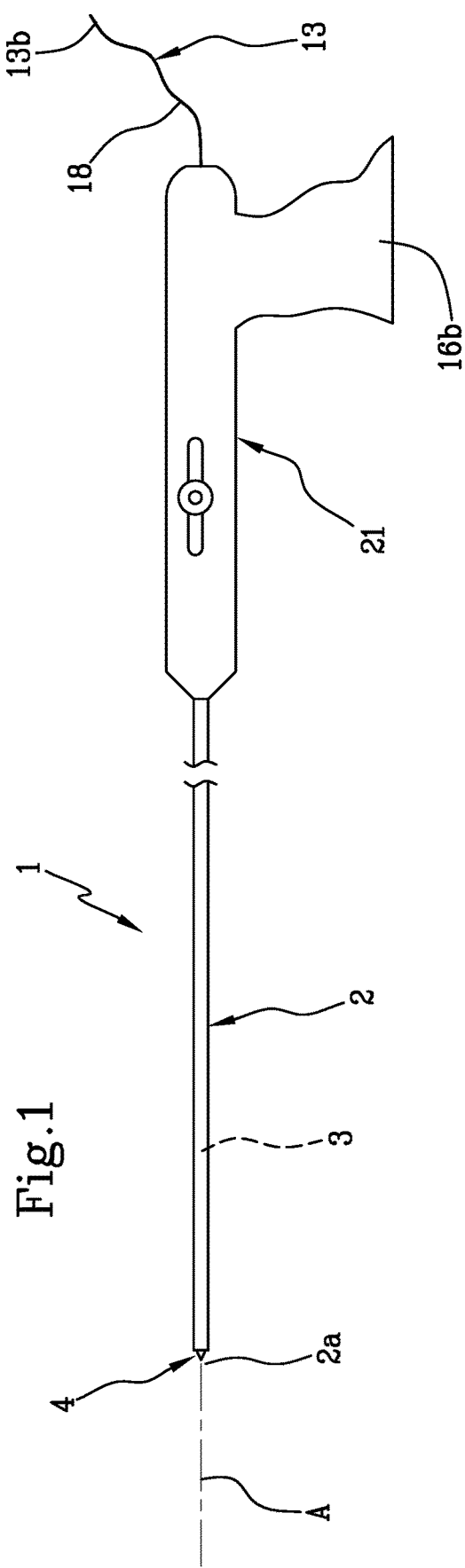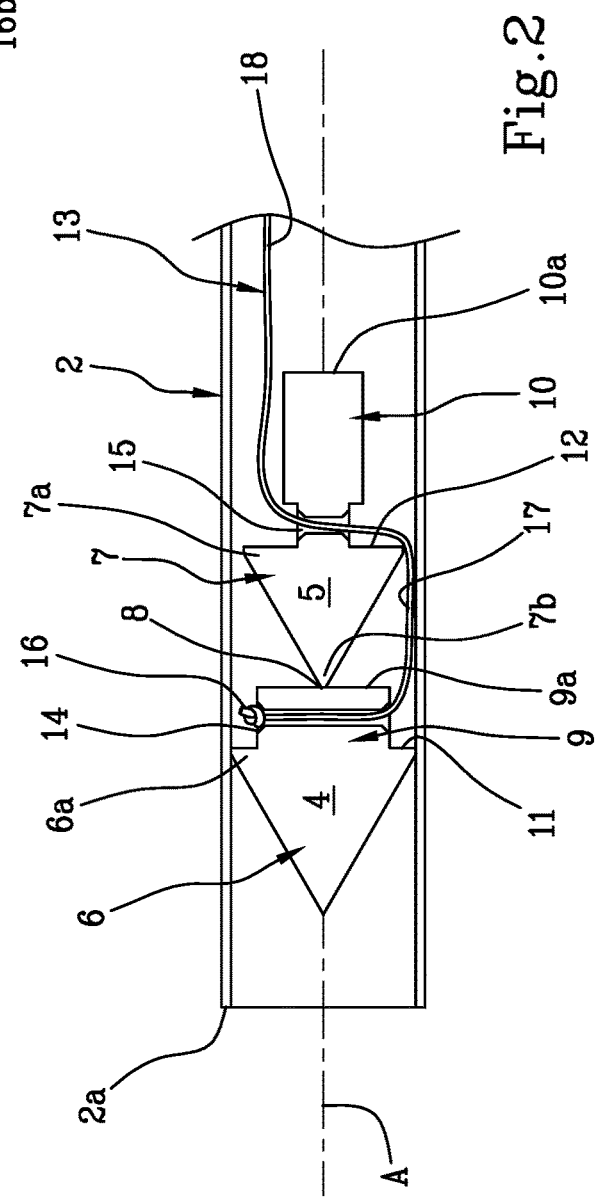

SUTURING DEVICE, IN PARTICULAR FOR SUTURING LACERATIONS OF THE MENISCUS

The present invention relates to a suturing device, in particular for suturing lacerations of the meniscus.

Consequently, the present invention applies in particular to the medical and biomedical field, particularly the design and production of instruments for arthroscopic surgery.

In fact, one of the most common orthopedic operations consists of repairing meniscal lacerations, in particular lacerations originating on the sides of the meniscus, which require suturing in good time to prevent them from growing and the consequent detachment of parts of the meniscus.

Instruments are known in the prior art for repairing meniscal lacerations in arthroscopy, some of which allow said lacerations to be sutured rapidly and with extreme precision.

One of the most popular methods for carrying out said operations is marketed by the company Smith&Nephew® and involves the use of a grooved needle slidably inserted into a cannula, associated with a surgical thread and two implants or retaining bodies.

In particular, the first and the second implant are defined by respective small metal plates arranged in sequence along the needle and slidably constrained to it; both of such plates are associated with the surgical thread. As regards the operation, the surgeon inserts the cannula into the patient's knee at a fixed angle and uses special manoeuvring means to move the needle so as to perforate the meniscus in two points on opposite sides of the laceration (in a transversal or longitudinal direction).

After each perforation, one of the aforesaid implants is released (again using the manoeuvring means) outside the meniscus so as to define a stop element, allowing the surgical thread to be tensioned over the laceration, suturing it.

For said reason, the surgical thread comprises at least one portion wound in a circle and tied with a sort of slipknot between the two implants, so that after they have both been arranged on the outer side of the meniscus, a traction of the free end of the thread results in a "pulley" effect on said ring portion, making it possible to close the wound by bringing the edges together.

Note that the plates have a substantially rectangular shape and are housed in the cutting needle (and in the cannula), in other words so that their lying plane is parallel to the development direction of the cannula.

Therefore, the "short" side of each plate displays a size suitable for being housed inside the sleeve and a sufficiently extended "long" side for distributing the strain on the meniscus without causing overpressure points near the wound.

Therefore, after being released, said plates tend to rotate on the plane so that their flat face stops at the meniscus.

Disadvantageously, said solution presents several inconveniences, both related to the structure of the plates and the arrangement of the thread. Firstly, the flat shape of the plates means that considerable strain is placed on their perimeter, consequently risking further injuries to the meniscus. Moreover, despite being remote, the possibility of the plate stopping at the meniscus in a configuration which is not perfectly planar, makes the device assembly phase critical.

Furthermore, the need to move the plates in a linear manner substantially obliges the producer to use a grooved needle, which acts as a guide/track for the plate itself, making it necessary to introduce the cannula to keep the implants and the thread isolated from the outside environment.

Additionally, the fact that the needle takes up a preponderant portion of the space inside the cannula, making it unusable for other purposes, considerably limits the size of thread which can be used, typically no larger than a 2-0 on the USP scale.

Disadvantageously, the use of such thin surgical thread increases the concentration of the strain afterwards and risks causing a cutting effect during traction.

Such consideration is even more valid if we consider the "pulley effect" that is created after the traction of the thread caused by the presence of the ring and "slipknot", wherein a plurality of sections of the thread run along the tissues with the risk of damaging them.

A further device for suturing lacerations of the meniscus is known from the publication AU2015202757, wherein the implants are defined by the surgical thread itself, in particular by sections of the same tied in a knot so that after traction they become compact and define a ball, which can define a stop element.

Despite being an interesting theory, said solution has the disadvantage of making the construction of the device complex and its manoeuvrability critical because tractions or thrusts in imprecise moments could result in a compaction or incorrect knotting of the thread.

Consequently it is the object of the present invention to provide a suturing device, in particular for suturing of lacerations of the meniscus, capable of overcoming the abovementioned inconveniences of the prior art.

In particular, it is an object of the present invention to provide a high-performance suturing device, which is simple to make.

Moreover, a further object of the present invention is to provide a safe and reliable suturing device.

Said objects are achieved by means of a suturing device, in particular for suturing lacerations of the meniscus, displaying the features of one or more of the subsequent claims, in particular comprising an elongated body provided with a longitudinal cavity extending along a main direction, at least a first and a second implant, slidably inserted in said cavity in sequence along said main direction and a surgical thread slidably inserted in said cavity and connected to said first and second implant.

According to one aspect of the present invention, the first and second implant comprise a first and a second wedge-shaped element respectively, arranged in sequence and extending from an enlarged portion to a tapered portion along said main direction.

Advantageously, in this way, the penetration of the tissues is carried out directly by the implant, reducing the size of the laceration and without requiring the use of needles.

Furthermore, the tapered portion of the second wedge-shaped element is preferably rigidly connected to the first implant, which advantageously makes it possible to simplify the implant handling system to a maximum because the piloting of just the second implant is sufficient to achieve the handling of both.

In this regard, note in particular that the tapered end of the second wedge-shaped element is rigidly connected to the first implant via a respective breakable connection area.

The breakable connection area preferably defines a weakened portion configured to tear as a result of a traction and/or torsion of the second implant in relation to the first one.

Advantageously, this reduces the production and assembly costs of the device, wherein it is sufficient to realise and apply just one monolithic element defining both of the implants.

These features and the relative technical advantages will nonetheless become apparent from the following description given by way of example, and consequently not limiting, of a preferred, therefore not exclusive, embodiment of a suturing device, in particular for suturing lacerations of the meniscus as illustrated in the accompanying drawing tables, wherein:

FIG. 1 shows a schematic view of a suturing device, in particular for suturing lacerations of the meniscus according to the present invention;

FIG. 2 shows a schematic section view of a part of the device in FIG. 1;

Figure 3:
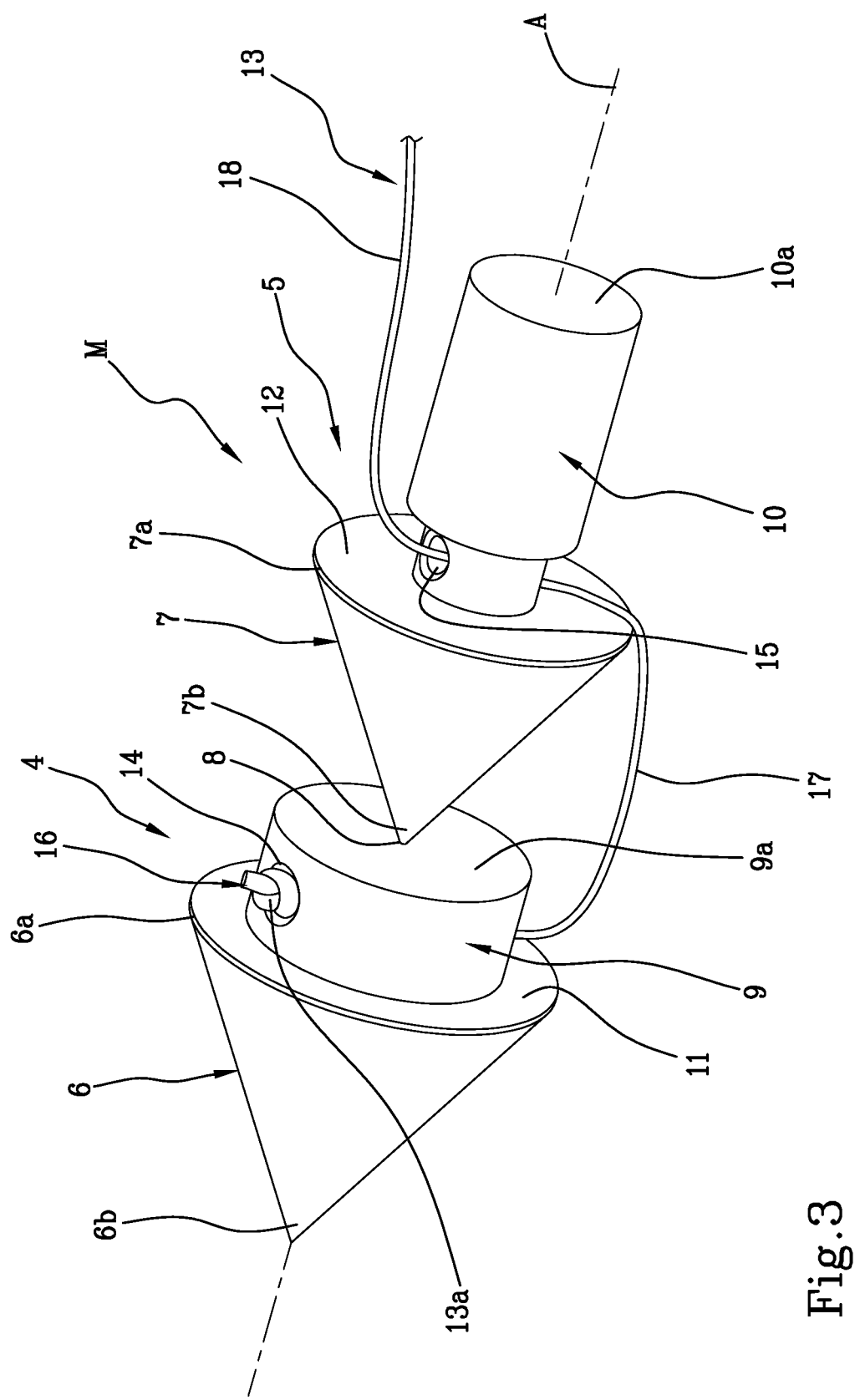
FIG. 3 shows a detail of the suturing device, in particular for suturing lacerations of the meniscus according to the present invention.
Figure 4:
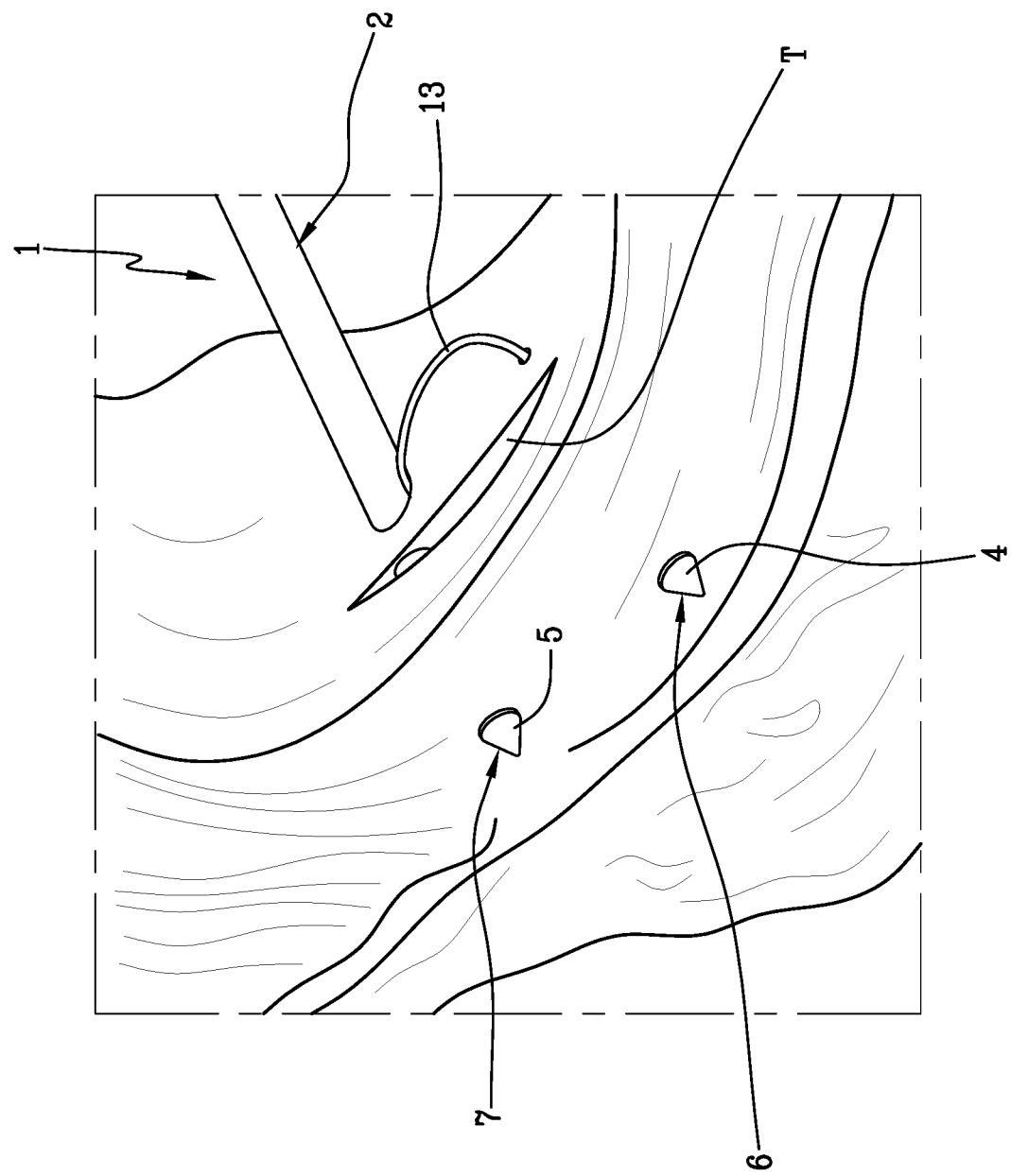
FIG. 4 shows a perspective view of a suturing device, in particular for suturing lacerations of the meniscus, during use.

With reference to the accompanying figures, the numeral 1 indicates a suturing device, in particular for suturing lacerations of the meniscus, according to the present invention.

Therefore, the device 1 principally applies to the orthopedic sector, preferably in arthroscopy operations or with a semi-open repair technique of the meniscus.

Said device comprises at least one elongated body 2 extending along a main direction "A" and is provided with a longitudinal cavity 3.

The elongated body 2 presents a first end portion 2a, operative, and a second end portion 2b, preferably connected to a handle of the device 1. Note that the first end portion 2a can present a rectilinear orientation, aligned with the remaining part of the elongated body 2, or curved, with a variable angle depending on the requirements of the surgeon and the laceration area to be sutured.

Preferably, the elongated body 2 is substantially a tube 20 and the longitudinal cavity 3 is a through type, also extending along the main direction "A" between a first opening arranged at the first end portion 2a and a second opening arranged at the second end portion 2b.

The cavity 3 is consequently a duct that is closed laterally by the wall of the needle and accessible from the openings.

Note that the tube 20 is preferably of a traditional type, in other words provided with a first end portion 2a (or free end) defined by a circular section orthogonal to is main direction "A".

A first 4 and a second implant 5 are housed (or housable), as well as a surgical thread 13 inside the elongated body 2, in particular inside the cavity 3.

The implants 4, 5 are bodies shaped to define a stop element able to abut against the outer wall of the meniscus during the traction of the thread 13. Such first 4 and second implant 5 are preferably slidably inserted inside the longitudinal cavity 3 of the elongated body 2.

More preferably, the first 4 and the second implant 5 are completely contained within the cavity 3 of the elongated body 2.

Moreover, said implants 4, 5 are arranged in sequence along the main direction "A".

According to one aspect of the present invention, the first 4 and the second implant 5 comprise, respectively, a first 6 and a second wedge-shaped element 7 arranged in sequence and extending from an enlarged portion 6a, 7a to a tapered portion 6b, 7b along said main direction "A".

More precisely, the tapered portion 6b, 7b of both of the wedge-shaped elements 6, 7 is substantially a sharp area, in other words tapered, therefore a true point.

Advantageously, in this way, it is the wedge-shaped element 6, 7 itself, which can act as a perforating member to penetrate the tissues of the meniscus, without requiring the use of needles and limiting the size of the incisions.

The first 6 and second wedge-shaped element 7 preferably present a conical shape.

Therefore, the tapered portion 6b, 7b is defined by the top of the cone, while the enlarged portion 6a, 7a constitutes its base.

Moreover, the first 4 and the second implant 5, and consequently the first 6 and the second wedge-shaped element 7, are preferably integrally formed, defining a monolithic element "M".

Advantageously, this reduces the production and assembly costs of the device, wherein it is sufficient to realise and apply just one monolithic element defining both implants.

In order to maximise performance and reduce costs, the implants 4, 5 are preferably realised in polymeric material, preferably PEEK or similar.

In this regard, note that the tapered portion 7b of the second wedge-shaped element 7 is rigidly connected to the first implant 4 via a respective breakable connection area 8.

Advantageously, this allows the two implants 4, 5, which are initially handled simultaneously, to be separated in a simple and efficient manner.

In this regard, the breakable connection area 8 is preferably substantially punctiform.

In the preferred embodiment, the breakable connection area 8 defines a weakened portion configured to tear as a result of a traction and/or torsion of the second implant 5 in relation to the first 4 (or vice versa).

Advantageously, in this way, the surgeon simply has to position the first implant 4 so that the respective enlarged portion abuts on the outer side of the meniscus, subsequently pulling the device towards him to break the link between the two implants 4, 5, in other words breaking the breakable connection area 8.

The first 4 and the second implant 5 preferably comprise a first 9 and a second tail 10 respectively, both protruding away from the respective wedge-shaped element 6, 7.

More precisely, each tail (first 9 or second 10) extends from the enlarged portion 6a, 7a of the respective wedge-shaped element 6, 7 to a relative end portion 9a, 10a.

Note that each tail 9, 10 has a transversal dimension smaller than that of the corresponding enlarged portion 6a, 7a, so as to define with it an abutment shoulder 11, 12.

The tails 9, 10 preferably present a substantially cylindrical shape and are substantially coaxial to the respective wedge-shaped element 6, 7 in the preferred embodiments.

Therefore, the shoulders 11, 12 preferably present an annular shape to distribute the strain uniformly on the side of the meniscus, so as to prevent the implants from damaging it near the channel through which the surgical thread 13 passes.

Note that the breakable connection area 8 between the two implants 4, 5, as well as the weakened portion, is preferably defined between the tapered portion 7b of the second implant 5 and the end portion 9a of the first tail 9. Therefore, the tapered portion 7b of the second wedge-shaped element 7 is rigidly connected to the end portion 9a of the first tail 9.

Each tail 9, 10 also comprises at least one portion for housing 9b, 10b the surgical thread 13.

In the preferred embodiment, such housing area 9b, 10b is defined by a through transversal opening 14, 15 made in each tail 9, 10.

Advantageously, in this way, it is possible to constrain the thread 13 to the implants 4, 5 in a simple manner, passing the thread 13 inside the opening 14, 15.

The thread 13, in turn, preferably comprises a first end portion 13a passing inside the respective opening 14 of the first tail 9 and provided with at least one stop element 16 that prevents it from coming out.

The stop element 16 is preferably defined by a knot or by a plate/sphere associated with the end portion 13a.

Moreover, the thread 13 extends from the first 13a to a second end portion 13b, in use projecting externally to an end opposite a point of the elongated body 2, in other words projecting externally to the second end portion 2b. More specifically, the thread 13 comprises a first suturing section 17, interposed between the first 4 and the second implant 5, having a variable length, and a second traction section 18, which extends between the second implant 5 and the second end portion 13b.

The second end portion 13b can preferably be held by the surgeon for performing traction of the thread 13, allowing it to run in relation to the second implant 5 reducing the length of the first section 17 to suture the laceration.

Note that the thread 13 preferably has no knot in the first section 17 (except in the case of a knot defining the stop element 16).

Moreover, the second section 18 preferably also has no sliding knots near the two implants, thus simplifying the structure of the device.

The enlarged portion 7a of the second wedge-shaped element 7 preferably has a transverse extension to the main direction "A" (i.e. the width) smaller than that of the enlarged portion 6a of the first wedge-shaped element 6 in order to allow the passage of the surgical thread 13.

Consequently, in the preferred embodiment, the enlarged portion 7a of the second wedge-shaped element 7 has a smaller diameter than that of the enlarged portion 6a of the first wedge-shaped element 6.

The first wedge-shaped element 6 is therefore preferably substantially counter-shaped with respect to the elongated body 2, in other words to the tube 20 (at least the transversal section of the enlarged portion 7a is).

On the contrary, the enlarged portion 7a of the second wedge-shaped element 7, when the latter is constrained to the first wedge-shaped element 6, defines an annular space 19 with the cavity 3 of the elongated body 2, through which the surgical thread 13 passes and runs.

Handling means 21, associated with the second end portion 2b of the elongated body 2, are provided for the first 4 and the second implant 5 configured to translate each implant 4, 5 from a resting position, wherein it is housed inside the cavity 3 of the elongated body (or partially projecting, see FIG. 1), to an operative position.

Therefore, the handling means 20 comprise at least one actuating member, which can be manoeuvred by a user and, preferably, a handle 21a.

The invention achieves the set objects and provides important advantages. In fact, the use of two wedge-shaped implants, arranged in sequence, offers easy handling of the implants, using their tapered shape as a perforating element, consequently not requiring the use of a needle.

Moreover, the monolithic construction of the two implants significantly simplifies their handling because the surgeon simply has to act on the second implant to pilot them both, making the device as simple to make as it is reliable.

Additionally, the use of two implants thus conformed substantially eliminates the need to prepare sliding knots between the two implants, consequently also facilitating the manoeuvrability of the device during operation.

The invention claimed is:

1. A meniscus suturing device, comprising:
an elongated body provided with a longitudinal cavity extending along a main direction;
at least a first and a second implant both slidably inserted within said cavity and arranged in sequence along said main direction so as to translate each from a resting position, wherein the at least first or second implant is housed inside the cavity of the elongated body, to an operative position; and
a surgical thread slidably inserted in said cavity and connected to said at least first and second implant;
wherein said at least first and second implant comprise, respectively, an at least a first and a second wedge-shaped element arranged in sequence and wherein each wedge-shaped element extends from an enlarged portion to a tapered portion along said main direction,
wherein said at least first and second implant are integrally formed, defining a monolithic element, and the tapered portion of the second wedge-shaped element is rigidly connected to the first implant via a respective breakable connection area,
wherein the at least first and second implant comprise, respectively, at least a first and a second tail protruding away from the respective enlarged portion of each wedge-shaped element to a relative end portion, and each tail presents a transverse dimension smaller than a transverse dimension of said enlarged portion of each respective wedge-shaped portion so as to define an abutment shoulder,
wherein the surgical thread is housed in the at least first and second implant and wherein the housing is only within the tail of each of the at least first and second implants, respectively,
wherein the at least first and second tail remain each rigidly connected to the corresponding at least first and second wedge-shaped element both in the resting and in the operative position.

2. The suturing device according to claim 1, wherein the tapered portion of the second wedge-shaped element is rigidly connected to the end portion of the first tail via said breakable connection area.

3. The suturing device according to claim 1, wherein said breakable connection area defines a weakened portion configured to tear as a result of a traction and/or torsion of the second implant in relation to the first implant.

4. The suturing device according to claim 1, wherein the enlarged portion of the second wedge-shaped element presents a transverse dimension smaller than a transverse dimension of the enlarged portion of the first wedge-shaped element in order to allow a passage of the surgical thread.

5. The suturing device according to claim 1, wherein said elongated body is a tube exhibiting a free end defined by a circular section orthogonal to a main direction of the elongated body.

6. The suturing device according to claim 1, wherein said first and second implant are realized in polyether ether ketone (PEEK).

* * * * *